(12) United States Patent
Ofuji et al.

(10) Patent No.: US 9,277,896 B2
(45) Date of Patent: Mar. 8, 2016

(54) RADIATION DETECTION APPARATUS AND RADIATION DETECTION SYSTEM

(71) Applicant: CANON KABUSHIKI KAISHA, Tokyo (JP)

(72) Inventors: Masato Ofuji, Takasaki (JP); Minoru Watanabe, Honjo (JP); Keigo Yokoyama, Honjo (JP); Jun Kawanabe, Kumagaya (JP); Kentaro Fujiyoshi, Tokyo (JP); Hiroshi Wayama, Saitama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/607,264

(22) Filed: Jan. 28, 2015

(65) Prior Publication Data

US 2015/0234056 A1    Aug. 20, 2015

(30) Foreign Application Priority Data

Feb. 14, 2014    (JP) ................................. 2014-026896
Jan. 7, 2015    (JP) ................................. 2015-001889

(51) Int. Cl.
| G01T 1/20 | (2006.01) |
| A61B 6/00 | (2006.01) |
| G01T 1/24 | (2006.01) |
| G01T 1/29 | (2006.01) |
| H01L 27/146 | (2006.01) |

(52) U.S. Cl.
CPC ............. *A61B 6/4233* (2013.01); *G01T 1/2018* (2013.01); *G01T 1/2928* (2013.01); *H01L 27/14663* (2013.01)

(58) Field of Classification Search
CPC ............ A61B 6/4233; H01L 27/14663; G01T 1/2928; G01T 1/2018
USPC ....................................................... 250/361 R
See application file for complete search history.

(56) References Cited

U.S. PATENT DOCUMENTS

| 7,205,547 B2 | 4/2007 | Ishii et al. |
| 7,205,568 B2 | 4/2007 | Watanabe et al. |
| 7,381,965 B2 | 6/2008 | Ishii et al. |
| 7,408,167 B2 | 8/2008 | Kameshima et al. |
| 7,435,968 B2 | 10/2008 | Watanabe et al. |
| 7,465,933 B2 | 12/2008 | Ishii et al. |

(Continued)

FOREIGN PATENT DOCUMENTS

JP    2013-012697    1/2013

*Primary Examiner* — David Porta
*Assistant Examiner* — Gisselle Gutierrez
(74) *Attorney, Agent, or Firm* — Fitzpatrick, Cella, Harper & Scinto

(57) ABSTRACT

A radiation detection apparatus includes conversion elements including a first electrode, a semiconductor layer, and a second electrode that are divided for each pixel; switching elements electrically connected to the first electrodes; and a first insulating layer that separates the conversion elements of adjacent pixels. The semiconductor layer is located between the first and second electrodes. A periphery of the semiconductor layer is located outside peripheries of the first and second electrodes. The semiconductor layer includes a first impurity semiconductor layer, a second impurity semiconductor layer, and an intrinsic semiconductor layer located between the first and second impurity semiconductor layers. Parameters of the apparatus are defined to set a residual charge 10 µs after the switching element is turned on to be not higher than 2%.

12 Claims, 11 Drawing Sheets

(56) References Cited

U.S. PATENT DOCUMENTS

| | | |
|---|---|---|
| 7,470,908 B2 | 12/2008 | Ishii et al. |
| 7,476,027 B2 | 1/2009 | Takenaka et al. |
| 7,488,948 B2 | 2/2009 | Ishii et al. |
| 7,535,506 B2 | 5/2009 | Nomura et al. |
| 7,541,617 B2 | 6/2009 | Mochizuki et al. |
| 7,573,038 B2 | 8/2009 | Yokoyama et al. |
| 7,573,041 B2 | 8/2009 | Kameshima et al. |
| 7,629,564 B2 | 12/2009 | Mochizuki et al. |
| 7,642,517 B2 | 1/2010 | Ishii et al. |
| 7,645,976 B2 | 1/2010 | Watanabe et al. |
| 7,750,422 B2 | 7/2010 | Watanabe et al. |
| 7,791,034 B2 | 9/2010 | Kameshima et al. |
| 7,812,313 B2 | 10/2010 | Mochizuki et al. |
| 7,812,317 B2 | 10/2010 | Watanabe et al. |
| 7,839,977 B2 | 11/2010 | Kameshima et al. |
| 7,850,367 B2 | 12/2010 | Takenaka et al. |
| 7,897,930 B2 | 3/2011 | Mochizuki et al. |
| 7,923,695 B2 | 4/2011 | Ishii et al. |
| 7,965,817 B2 | 6/2011 | Kameshima et al. |
| 7,989,772 B2 | 8/2011 | Yagi et al. |
| 8,067,743 B2 | 11/2011 | Ishii et al. |
| 8,084,745 B2 | 12/2011 | Mochizuki et al. |
| 8,154,641 B2 | 4/2012 | Nomura et al. |
| 8,167,486 B2 | 5/2012 | Takenaka et al. |
| 8,222,611 B2 | 7/2012 | Yagi et al. |
| 8,368,027 B2 | 2/2013 | Ishii et al. |
| 8,519,344 B2 | 8/2013 | Ishii et al. |
| 8,680,472 B2 | 3/2014 | Mochizuki et al. |
| 8,866,093 B2 | 10/2014 | Fujiyoshi et al. |
| 2007/0272870 A1* | 11/2007 | Ishii ................ G01T 1/24 250/370.08 |
| 2012/0305785 A1 | 12/2012 | Fujiyoshi et al. ....... 250/370.08 |

\* cited by examiner

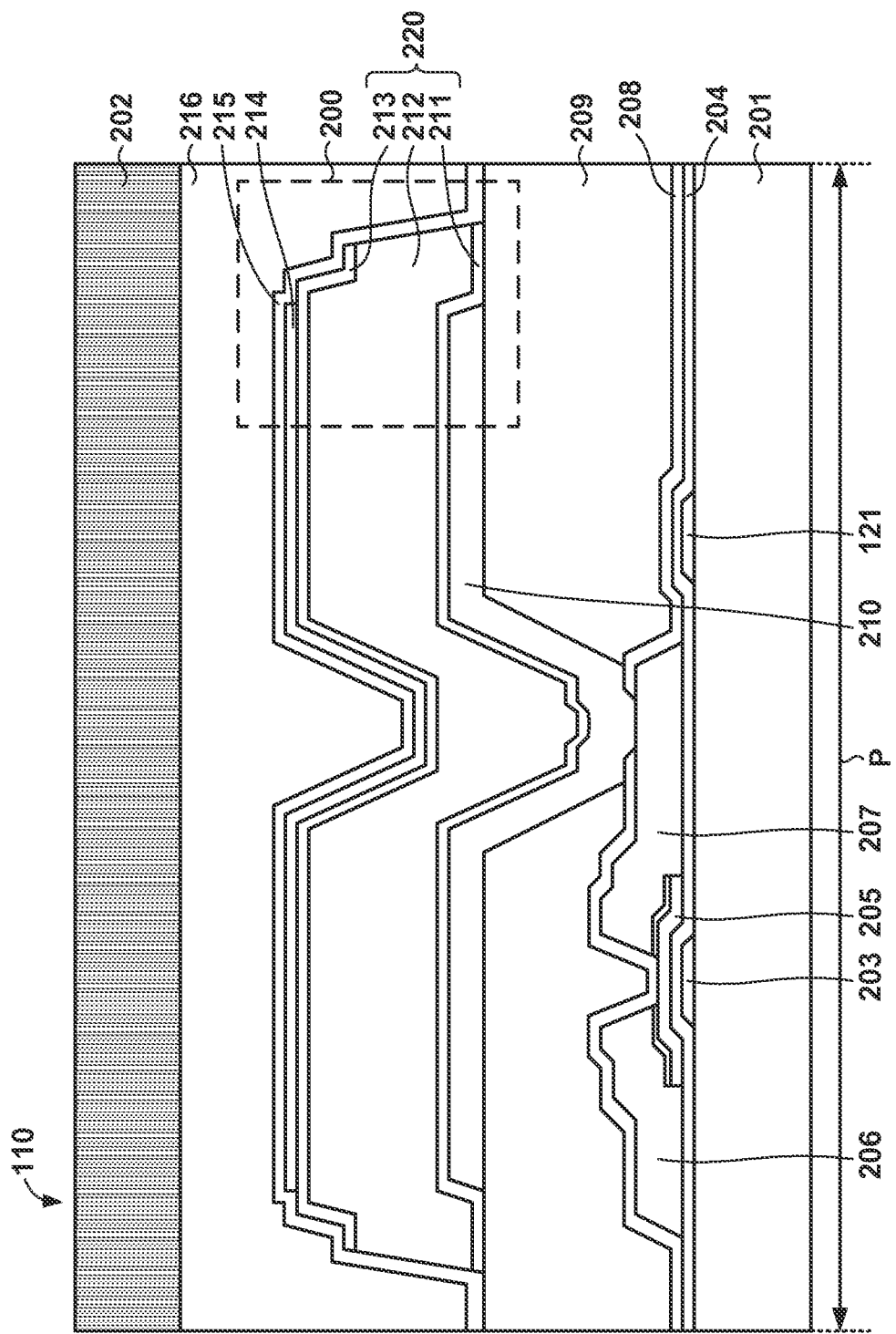

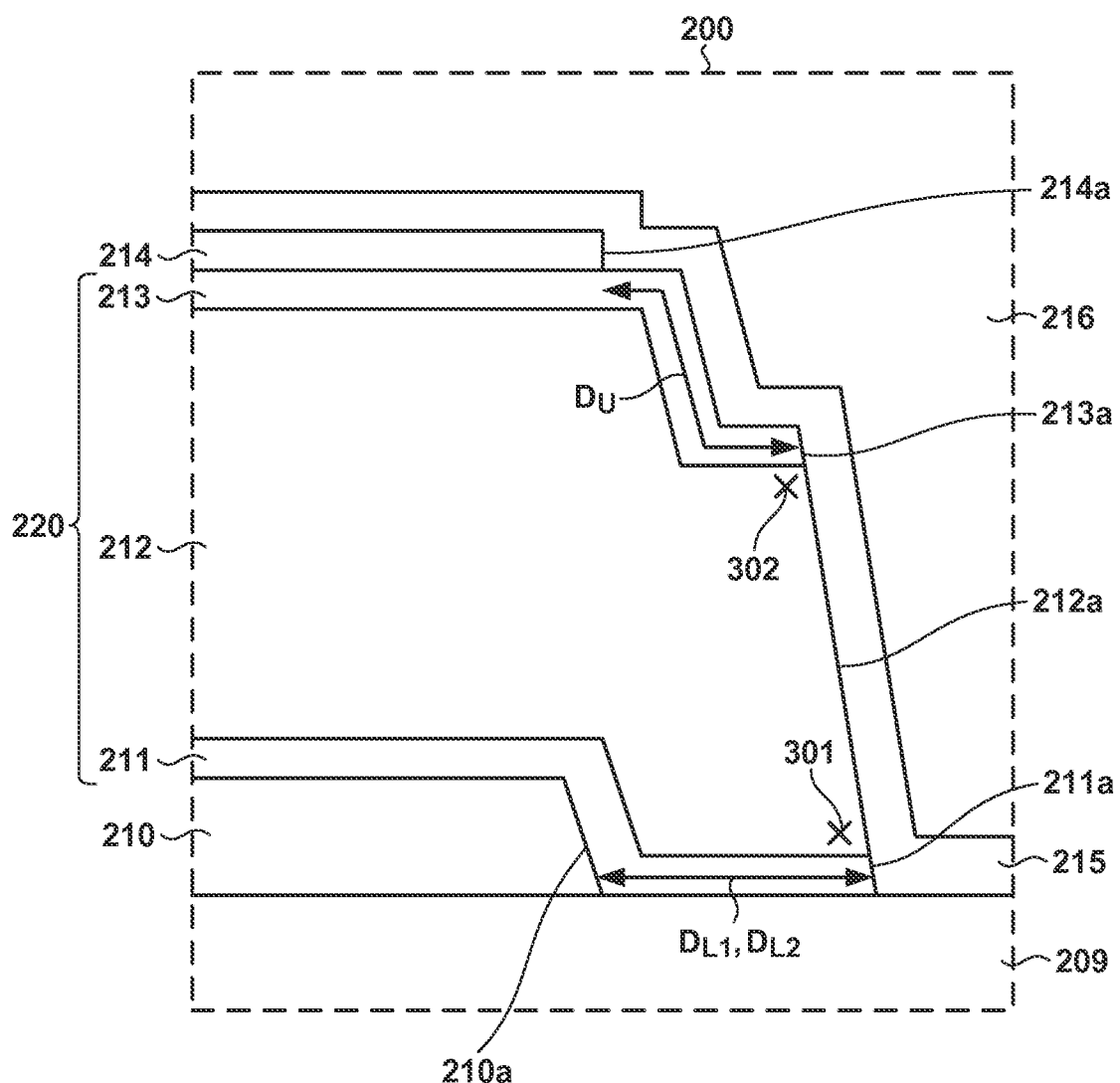

FIG. 4

| | RADIATION DETECTION APPARATUS 100 | FIRST COMPARATIVE EXAMPLE | SECOND COMPARATIVE EXAMPLE |
|---|---|---|---|
| $R_{on}[\Omega]$ | 3.00E+05 | 3.00E+05 | 3.00E+05 |
| $P[\mu m]$ | 160 | 160 | 160 |
| $D_{L1}[\mu m]$ | 4.0 | 13.0 | 4.0 |
| $R_{\square L1}[\Omega]$ | 8.00E+07 | 8.00E+07 | 8.00E+07 |
| $D_U[\mu m]$ | 4.0 | 4.0 | 4.0 |
| $R_{\square U}[\Omega]$ | 6.70E+08 | 6.70E+08 | 5.00E+09 |
| $\{D_{L1}/(4 \times P)\} \times R_{\square L1}$ | 5.00E+05 | 1.63E+06 | 5.00E+05 |
| $\{D_{L1}/(4 \times P)\} \times R_{\square L1} < 5 \times R_{on}?$ | Yes | No | Yes |
| $\{D_U/(4 \times P)\} \times R_{\square U}$ | 4.19E+06 | 4.19E+06 | 3.13E+07 |
| $\{D_U/(4 \times P)\} \times R_{\square U} < 100 \times R_{on}?$ | Yes | Yes | No |
| RESIDUAL CHARGE | 1.2% | 3.3% | 2.9% |

FIG. 5

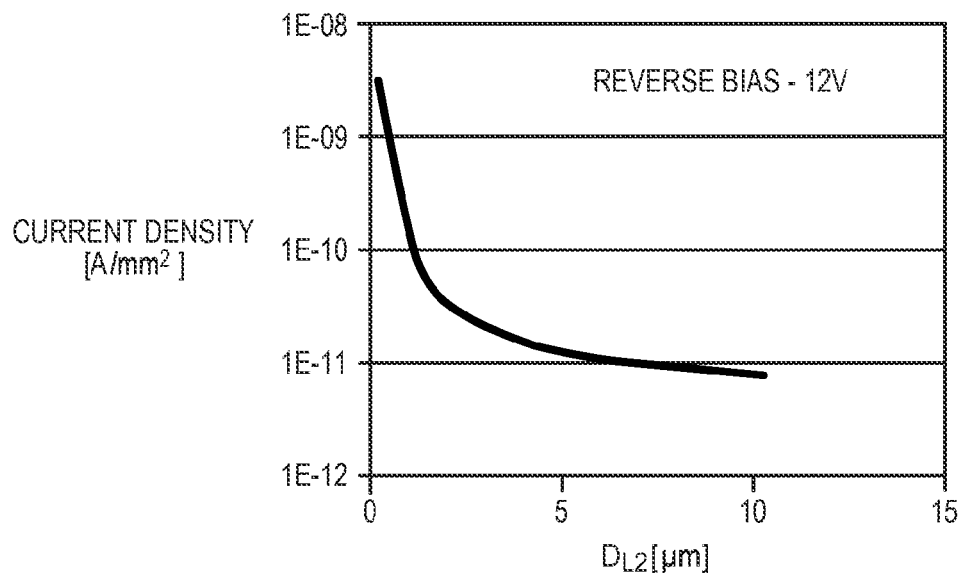

FIG. 7

|  | RADIATION DETECTION APPARATUS 600 | FIRST COMPARATIVE EXAMPLE | SECOND COMPARATIVE EXAMPLE |
|---|---|---|---|
| $R_{on}[\Omega]$ | 3.00E+05 | 3.00E+05 | 3.00E+05 |
| $P[\mu m]$ | 160 | 160 | 160 |
| $D_{L1}[\mu m]$ | 4.0 | 13.0 | 4.0 |
| $R_{\square L1}[\Omega]$ | 8.00E+07 | 8.00E+07 | 8.00E+07 |
| $D_U[\mu m]$ | 4.0 | 4.0 | 4.0 |
| $R_{\square U}[\Omega]$ | 6.70E+08 | 6.70E+08 | 5.00E+09 |
| $\{D_{L1}/(4\times P)\}\times R_{\square L1}$ | 5.00E+05 | 1.63E+06 | 5.00E+05 |
| $\{D_{L1}/(4\times P)\}\times R_{\square L1} < 5\times R_{on}$? | Yes | No | Yes |
| $\{D_U/(4\times P)\}\times R_{\square U}$ | 4.19E+06 | 4.19E+06 | 3.13E+07 |
| $\{D_U/(4\times P)\}\times R_{\square U} < 100\times R_{on}$? | Yes | Yes | No |
| RESIDUAL CHARGE | 1.3% | 3.5% | 2.7% |

FIG. 8

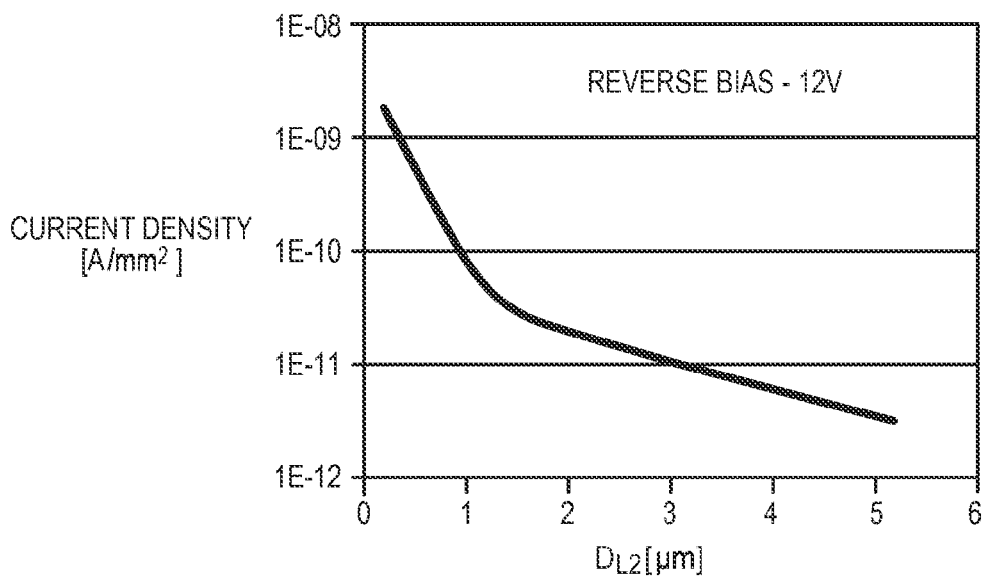

RADIATION DETECTION APPARATUS AND RADIATION DETECTION SYSTEM

BACKGROUND OF THE INVENTION

1. Field of the Invention

The present invention relates to a radiation detection apparatus and a radiation detection system.

2. Description of the Related Art

A radiation detection apparatus has been used, in which a plurality of pixels each having a combination of a conversion element and switching element are arranged. As the conversion element, a PIN diode or a MIS diode is used. In particular, a PIN structure in which a semiconductor layer is sandwiched between two electrodes can be easily manufactured, has a simple operation mechanism, and thus is widely used. By separating a semiconductor layer into islands for respective pixels, a sharp image with less crosstalk between pixels is obtained. However, in the structure in which the semiconductor layer is separated into islands, a leakage path is readily formed on the side wall of the semiconductor layer. The formation of the leakage path has adverse effects such as an increase in reverse dark current and a decrease in the dynamic range of the radiation detection apparatus. Japanese Patent Laid-Open No. 2013-012697 proposes a conversion element having a structure in which the periphery of a semiconductor layer is positioned outside the periphery of an electrode in order to suppress the formation of the leakage path on the side wall of the semiconductor layer.

SUMMARY OF THE INVENTION

In the radiation detection apparatus described in Japanese Patent Laid-Open No. 2013-012697, a residual charge readily occurs, which will be described later. An aspect of the present invention provides a technique for reducing the residual charge in a radiation detection apparatus having a conversion element in which the periphery of a semiconductor layer is positioned outside the periphery of an electrode.

According to some embodiments, a radiation detection apparatus including a plurality of pixels is provided. The apparatus comprises conversion elements including a first electrode, a semiconductor layer, and a second electrode that are divided for each pixel; switching elements electrically connected to the first electrodes; and a first insulating layer that separates the conversion elements of adjacent pixels. The semiconductor layer is located between the first electrode and the second electrode, a periphery of the semiconductor layer is located outside a periphery of the first electrode and a periphery of the second electrode, the semiconductor layer includes a first impurity semiconductor layer including a portion in contact with the first electrode, a second impurity semiconductor layer including a portion in contact with the second electrode, and an intrinsic semiconductor layer located between the first impurity semiconductor layer and the second impurity semiconductor layer, and a length $D_{L1}$ from a periphery of the first impurity semiconductor layer along the first impurity semiconductor layer up to the portion, in contact with the first electrode, of the first impurity semiconductor layer, a length $D_U$ from a periphery of the second impurity semiconductor layer along the second impurity semiconductor layer up to the portion, in contact with the second electrode, of the second impurity semiconductor layer, a sheet resistance $R_{\square L1}$ of the first impurity semiconductor layer, a sheet resistance $R_{\square U}$ of the second impurity semiconductor layer, a pixel pitch $P$ of the plurality of pixels, and an ON resistance $R_{on}$ of the switching element are defined to set a residual charge 10 μs after the switching element is turned on to be not higher than 2%.

Further features of the present invention will become apparent from the following description of exemplary embodiments (with reference to the attached drawings).

BRIEF DESCRIPTION OF THE DRAWINGS

FIG. 2 is a schematic sectional view of one pixel of the radiation detection apparatus in FIG. 1;

FIG. 3 is an enlarged view of part of FIG. 2;

FIG. 4 is a table for explaining the results of measuring the residual charge in various radiation detection apparatuses;

FIG. 5 is a graph for explaining the results of measuring a current density in various radiation detection apparatuses;

FIG. 7 is a table for explaining the results of measuring the residual charge in various radiation detection apparatuses;

FIG. 8 is a graph for explaining the results of measuring a current density in various radiation detection apparatuses;

DESCRIPTION OF THE EMBODIMENTS

Figure 1:
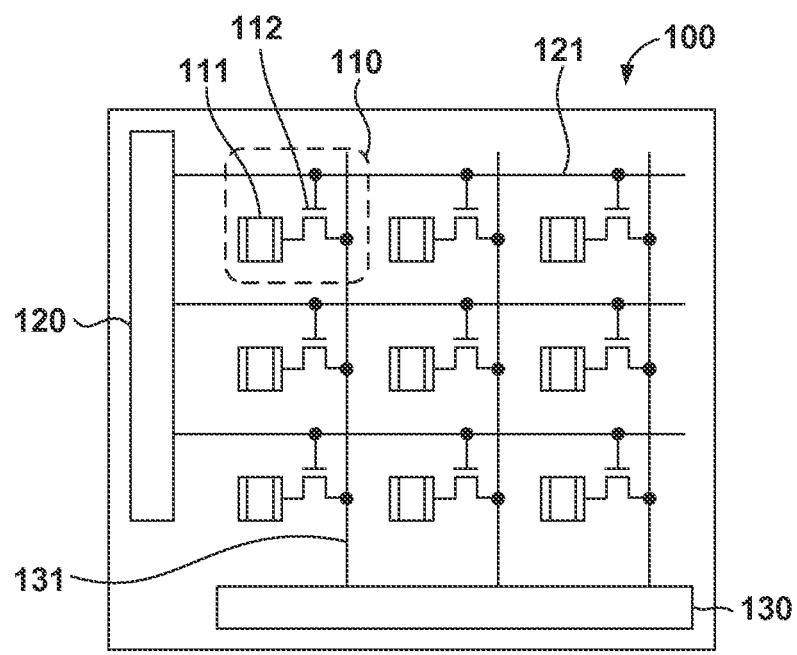
FIG. 1 is an equivalent circuit diagram of a radiation detection apparatus according to some embodiments.

Embodiments of the present invention will be described below with reference to the accompanying drawings. The same reference numerals denote the same components throughout various embodiments, and a repetitive description will be omitted. The embodiments can be appropriately changed and combined.

A radiation detection apparatus 100 according to some embodiments will be explained with reference to FIGS. 1 to 5. The radiation detection apparatus 100 is used for, for example, a medical image diagnostic apparatus, a nondestructive inspection apparatus, an analysis apparatus using radiation, or the like. FIG. 1 is a schematic equivalent circuit diagram of the radiation detection apparatus 100. The radiation detection apparatus 100 includes a plurality of pixels 110. The plurality of pixels 110 are arranged in a two-dimensional matrix to constitute a pixel array. Each pixel 110 includes a conversion element 111 and a switching element 112. The conversion element 111 is connected to a signal line 131 via the switching element 112. The radiation detection apparatus 100 includes a plurality of signal lines 131. Each signal line 131 is shared between the plurality of pixels 110 aligned in the column direction (vertical direction in FIG. 1). One end of the signal line 131 is connected to a readout circuit 130. The control terminal of the switching element 112 is connected to a driving line 121. The radiation detection apparatus 100 includes a plurality of driving lines 121. Each driving line 121 is shared between the plurality of pixels 110 aligned in the row direction (horizontal direction in FIG. 1). One end of the driving line 121 is connected to a driving circuit 120.

FIG. 2 is a schematic sectional view in which attention is paid to one pixel 110 in FIG. 1. This sectional view shows a section of the pixel 110 taken along a plane perpendicular to a substrate in a direction parallel to the row direction of the plurality of pixels 110. In the pixel array of the radiation detection apparatus 100, the arrangement in FIG. 2 is repetitively arranged in the two-dimensional matrix. The plurality of pixels 110 are formed on a substrate 201 made of an insulating material such as glass. The radiation detection apparatus 100 includes a scintillator layer 202 on the plurality of pixels 110. The scintillator layer 202 is made of caesium iodide (CsI), a gadolinium oxysulfide (GOS), or the like. The scintillator layer 202 converts a radiation into visible light that is light of a wavelength detectable by the conversion element 111. The radiation may enter the radiation detection apparatus 100 from the side (upper side in the drawing) of the scintillator layer 202 or from the side (lower side in the drawing) of the substrate 201. The driving circuit 120 and the readout circuit 130 may be formed on the substrate 201 and electrically connected to the pixel array via conductive patterns. Instead, the driving circuit 120 and the readout circuit 130 may be formed on a substrate different from the substrate 201 and electrically connected to the pixel array via conductive pads on the substrate 201.

The driving line 121, the signal line 131 (not shown in FIG. 2), and a gate electrode 203 are formed on the substrate 201, and an insulating layer 204 is formed on them. The driving line 121 and the gate electrode 203 are electrically connected. Of the insulating layer 204, a portion on the gate electrode 203 functions as a gate insulating film. A channel layer 205 is formed on the gate insulating film. One end of the channel layer 205 is covered with a source electrode 206, and the other end of the channel layer 205 is covered with a drain electrode 207. The source electrode 206 is electrically connected to the signal line 131. The source electrode 206 and the signal line 131 may be integrally constituted on the same conductive layer. The gate electrode 203, the gate insulating film, the channel layer 205, the source electrode 206, and the drain electrode 207 form a thin-film transistor (TFT). This TFT functions as the switching element 112 in FIG. 1. An impurity semiconductor layer may be formed as a contact layer between the channel layer 205 and the source electrode 206 and between the channel layer 205 and the drain electrode 207.

A protective layer 208 and a planarizing layer 209 are sequentially formed on the above-mentioned thin-film transistor, the driving line 121, and the signal line 131. The protective layer 208 is an inorganic insulating film of SiN or the like. The planarizing layer 209 is an organic insulating film of acrylic, polyimide, or the like. The protective layer 208 and the planarizing layer 209 have openings above the drain electrode 207. The upper surface of the planarizing layer 209 is flat except for the opening.

A first electrode 210, a first impurity semiconductor layer 211, an intrinsic semiconductor layer 212, a second impurity semiconductor layer 213, a second electrode 214, a protective layer 215, and a planarizing layer 216 are sequentially formed on the planarizing layer 209. The first impurity semiconductor layer 211, the intrinsic semiconductor layer 212, and the second impurity semiconductor layer 213 will be called a semiconductor layer 220 as a whole. The semiconductor layer 220 is made of, for example, amorphous silicon (a-Si). The first electrode 210, the semiconductor layer 220, and the second electrode 214 form a PIN photodiode. This photodiode functions as the conversion element 111 in FIG. 1. The first electrode 210 is divided for each pixel 110. That is, the first electrodes 210 of the adjacent pixels 110 are separated from each other. The first impurity semiconductor layer 211, the intrinsic semiconductor layer 212, the second impurity semiconductor layer 213, and the second electrode 214 are also divided for each pixel 110. The protective layer 215 and the planarizing layer 216 are arranged commonly for the plurality of pixels 110. The conversion elements 111 of the adjacent pixels 110 are separated from each other by the protective layer 215 and the planarizing layer 216. The protective layer 215 is an inorganic insulating film of SiN or the like. The planarizing layer 216 is an organic insulating film of acrylic, polyimide, or the like. The upper surface of the planarizing layer 216 is flat.

Part of the first electrode 210 is buried in the opening of the protective layer 208 and the opening of the planarizing layer 209, and is joined to the drain electrode 207. The second electrode 214 is connected to a bias line (not shown). A bias voltage for performing photoelectric conversion by the conversion element 111 is applied to the second electrode 214 via the bias line. The first impurity semiconductor layer 211 and the second impurity semiconductor layer 213 have different conductivity types. In the following description, the first impurity semiconductor layer 211 is of an $n^+$ type, and the second impurity semiconductor layer 213 is of a $p^+$ type, but the conductivity types may be exchanged. The first impurity semiconductor layer 211 functions as a blocking layer that prevents injection of holes from the first electrode 210 to the intrinsic semiconductor layer 212. The second impurity semiconductor layer 213 functions as a blocking layer that prevents injection of electrons from the second electrode 214 to the intrinsic semiconductor layer 212. The intrinsic semiconductor layer 212 may be made of an impurity-free semiconductor, or an n- or p-type semiconductor lower in impurity concentration than the first impurity semiconductor layer 211 and the second impurity semiconductor layer 213.

The arrangement of the conversion element 111 will be explained in detail with reference to FIG. 3. FIG. 3 is an enlarged view of a region 200 in FIG. 2. The first impurity semiconductor layer 211, the intrinsic semiconductor layer 212, and the second impurity semiconductor layer 213 are divided by successively etching three semiconductor layers by using the same mask. Hence, a periphery 211a of the first impurity semiconductor layer 211, a periphery 212a of the intrinsic semiconductor layer 212, and a periphery 213a of the second impurity semiconductor layer 213 are positioned on the same plane to form the periphery of the semiconductor layer 220. In other words, the upper surface of the first impurity semiconductor layer 211 and the lower surface of the intrinsic semiconductor layer 212 coincide with each other, and the upper surface of the intrinsic semiconductor layer 212 and the lower surface of the second impurity semiconductor layer 213 coincide with each other.

The first impurity semiconductor layer 211 contacts the upper surface and side surface of the first electrode 210, and also contacts a portion, around the first electrode 210, of the planarizing layer 209. As a result, the periphery 211a of the first impurity semiconductor layer 211 is positioned outside a periphery 210a of the first electrode 210.

The second impurity semiconductor layer 213 contacts the lower surface of the second electrode 214, and also contacts a portion, around the second electrode 214, of the protective layer 215. As a result, the periphery 213a of the second impurity semiconductor layer 213 is positioned outside a periphery 214a of the second electrode 214.

The arrangement shown in FIG. 2 suppresses generation of a leakage path on the side surface of the semiconductor layer 220, and improves the fill factor (FF) and the sensitivity. However, the first impurity semiconductor layer 211 has a resistance value higher than that of the first electrode 210, so a parasitic resistance is generated in the first impurity semiconductor layer 211. Electrons generated near the periphery 212a (for example, a position 301) of the intrinsic semiconductor layer 212 are influenced by the parasitic resistance when they are collected to the first electrode 210. This causes the residual charge. A parasitic resistance is similarly generated even in the second impurity semiconductor layer 213. Holes generated near the periphery 212a (for example, a position 302) of the intrinsic semiconductor layer 212 are influenced by the parasitic resistance when they are collected to the second electrode 214. This also causes the residual charge.

In this embodiment, the conversion element 111 is formed to satisfy both the following inequalities (1) and (2) in order to reduce the residual charge:

$$\{D_{L1}/(4 \times P)\} \times R_{\square L1} < 5 \times R_{on} \quad (1)$$

$$\{D_U/(4 \times P)\} \times R_{\square U} < 100 \times R_{on} \quad (2)$$

In these inequalities, $D_{L1}$ is the length from the periphery 211a of the first impurity semiconductor layer 211 along the first impurity semiconductor layer 211 up to a portion, in contact with the first electrode 210, of the first impurity semiconductor layer 211. Among such lengths, a minimum length may be employed. $D_U$ is the length from the periphery 213a of the second impurity semiconductor layer 213 along the second impurity semiconductor layer 213 up to a portion, in contact with the second electrode 214, of the second impurity semiconductor layer 213. $R_{\square L1}$ is the sheet resistance of the first impurity semiconductor layer 211. $R_{\square U}$ is the sheet resistance of the second impurity semiconductor layer 213. $R_{on}$ [Ω] is the ON resistance of the switching element 112. P is the width (that is, pixel pitch: see FIG. 2) of one pixel 110. The left-hand side of inequality (1) represents the magnitude of the parasitic resistance of the first impurity semiconductor layer 211 at the portion of the length $D_{L1}$. The left-hand side of inequality (2) represents the magnitude of the parasitic resistance of the second impurity semiconductor layer 213 at the portion of the length $D_U$.

The residual charge when both inequalities (1) and (2) are satisfied will be examined with reference to FIG. 4. FIG. 4 shows experimental results when the radiation detection apparatus in which the parameters of inequalities (1) and (2) were set to various values was installed in a laboratory at room temperature (25° C.), and the residual charge 10 μs after the switching element 112 was turned on was measured. The residual charge was 1.2% in the radiation detection apparatus 100 satisfying both inequalities (1) and (2). The residual charge was 3.3% in the first comparative example in which inequality (2) was satisfied but inequality (1) was not satisfied. The residual charge was 2.9% in the second comparative example in which inequality (1) was satisfied but inequality (2) was not satisfied.

Generally in the radiation detection apparatus, the residual charge 10 μs after the switching element connected to the conversion element is turned on needs to be equal to or lower than 2%. An example of this reason will be explained below. Let r (%) be the residual charge 10 μs after the switching element 112 is turned on. Then, when simple exponential charge transfer is assumed, a transfer time constant τ (s) is given by:

$$\tau = -10 \times 10^{-6}/\ln(r/100) \quad (3)$$

When the radiation detection apparatus is operated at a frame frequency FR (fps), equation (4) is established:

$$FR = 1/T = 1/\{N(t_{sw} + t_{amp})\} \quad (4)$$

where variables in equation (4) are as follows:
T: frame period (s)
N: number of driving lines
$t_{sw}$: length (s) of the period necessary for charge transfer (=period in which the switching element is ON)
$t_{amp}$: period (s) necessary for charge amount measurement by the readout circuit Letting Th (%) be the residual charge $t_{sw}$ (s) after the switching element 112 is turned on, equation (5) is established:

$$t_{sw} = -\tau \cdot \ln(Th/100) \quad (5)$$

$$= 10 \times 10^{-6} \ln(Th/100)/\ln(r/100))$$

If r≤2%, the radiation detection apparatus can be operated at Th=1%, $t_{amp}$=20 μs, N=2100, and FR=15 fps. These values are those generally requested of the radiation detection apparatus. If the radiation detection apparatus 100 satisfies both inequalities (1) and (2), the residual charge 10 μs after the switching element connected to the conversion element is turned on can become equal to or lower than 2%.

If the periphery 210a of the first electrode 210 is brought close to the periphery of the semiconductor layer 220 in order to satisfy the aforementioned inequality (1), a leakage current readily increases under the influence of tunneling of holes from the first electrode 210 to the side surface of the semiconductor layer 220. In some embodiments, therefore, a length $D_{L2}$ from the periphery 210a of the first electrode 210 to the periphery of the semiconductor layer 220 is set to be equal to or larger than 5 nm. The length from the periphery 210a of the first electrode 210 to the periphery of the semiconductor layer 220 may be defined by a minimum distance from the periphery 210a of the first electrode 210 to the periphery of the semiconductor layer 220. As shown in FIG. 3, $D_{L1}$=$D_{L2}$ in the radiation detection apparatus 100.

In some embodiments, the length $D_{L2}$ is set to be equal to or larger than 1 μm. FIG. 5 shows the measurement result of the current density of a reverse dark current when the length $D_{L2}$ is changed variously. As shown in FIG. 5, if the length $D_{L2}$ is equal to or larger than 1 μm, the current density of the reverse dark current can be suppressed to be equal or lower than $10^{-10}$ A/mm².

Generally in the radiation detection apparatus, the current density of the reverse dark current needs to be equal to or lower than $10^{-10}$ A/mm². An example of this reason will be explained below. Letting A (m²/pixel) be the area of the conversion element, C1 (F/pixel) be the capacitance, and Vr (V) be the magnitude of a reverse bias to be applied to the conversion element, a saturated charge amount Qsat (C/pixel) of the conversion element is given by:

$$Q\text{sat} = C1 \cdot Vr \quad (6)$$

Assuming that a dark current Jdark (A/mm²) flows through the conversion element, a charge amount Qdark (C/pixel) accumulated in the conversion element during the frame period T (s) is given by:

$$Q\text{dark} = A \cdot J\text{dark} \cdot T \quad (7)$$

A case in which C1=1.7 (pF), Vr=12 (V), A=26,000 (μm²), and 1/T=15 (Hz) will be examined. In this case, if Jdark is equal to or smaller than 1.2×$10^{-10}$ (A/mm²), the loss (Qdark/

Qsat) of the dynamic range by the dark current can be suppressed to be equal to or lower than 1%. The dynamic range of the perception amount of the human eye is 1:100 to 1:1000. Thus, if the loss of the dynamic range is equal to or lower than 1%, degradation of the image quality by the loss of the dynamic range is hardly recognized.

For the same reason as that described above, the length from the periphery 214a of the second electrode 214 to the periphery of the semiconductor layer 220 may be set to be equal to or larger than 5 nm, or equal to or larger than 1 µm. The length from the periphery 214a of the second electrode 214 to the periphery of the semiconductor layer 220 may be defined by a minimum distance from the periphery 214a of the second electrode 214 to the periphery of the semiconductor layer 220.

In the above-described embodiment, an inversely staggered TFT using a semiconductor layer mainly made of amorphous silicon is adopted as the switching element 112. For example, a staggered TFT mainly made of polysilicon, an organic TFT, an oxide TFT, or the like may be used.

Figure 6:
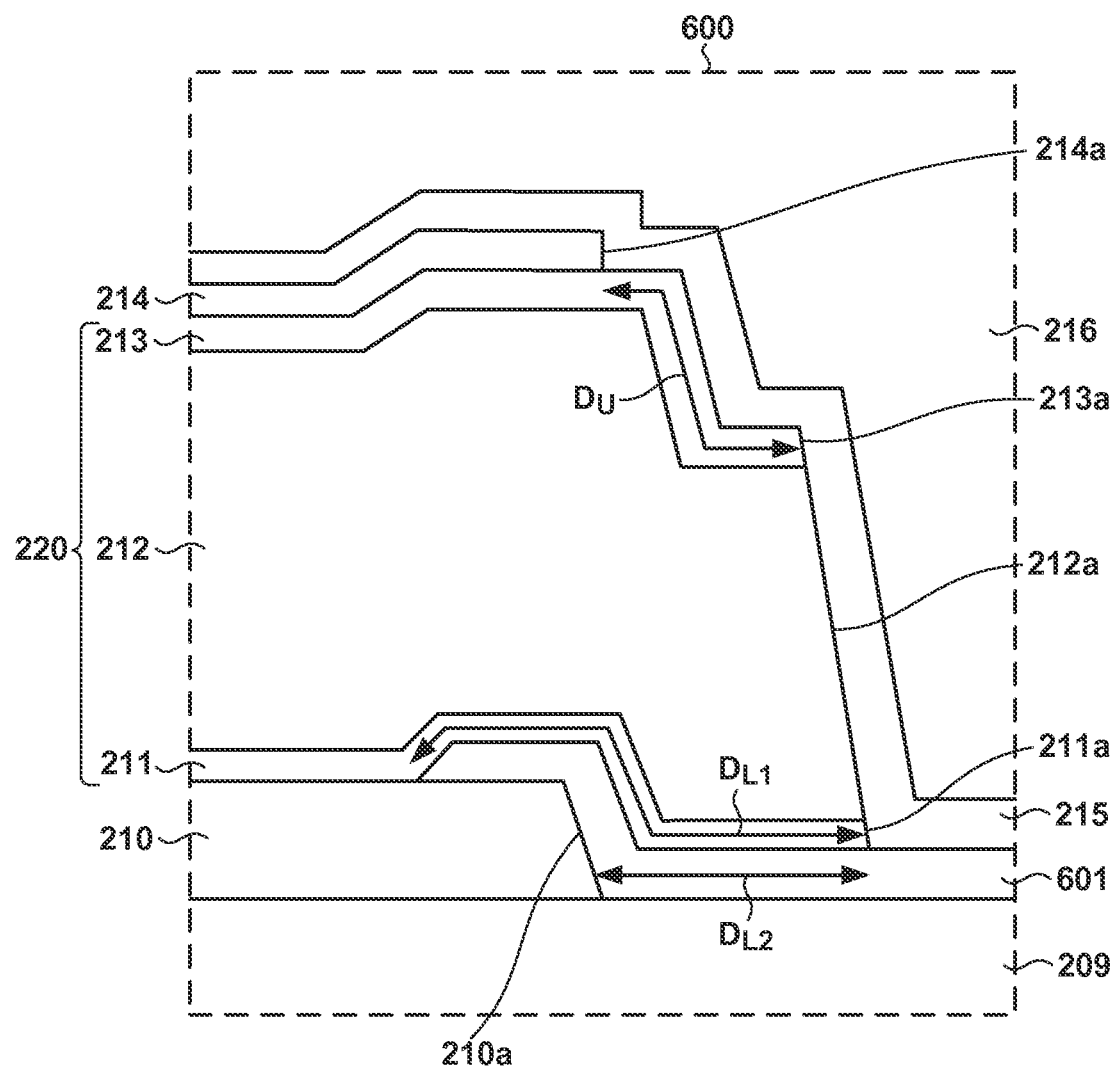
FIG. 6 is a partial schematic sectional view of one pixel of a radiation detection apparatus according to some embodiments.

A radiation detection apparatus 600 according to some embodiments will be explained with reference to FIGS. 6 to 8. FIG. 6 is a schematic sectional view showing a portion, corresponding to the region 200 in FIG. 3, of the radiation detection apparatus 600. The radiation detection apparatus 600 is different from the radiation detection apparatus 100 in the structure of the portion shown in FIG. 6. The remaining portion of the radiation detection apparatus 600 may be the same as that of the radiation detection apparatus 100, and a repetitive description will be omitted.

The radiation detection apparatus 600 further includes a protective layer 601. The protective layer 601 is, for example, an inorganic insulating film made of SiN or the like. The protective layer 601 covers the end portion of a first electrode 210. More specifically, the protective layer 601 contacts the end portion of the upper surface of the first electrode 210, the side surface of the second electrode, and a portion, uncovered by the first electrode 210, of the upper surface of a planarizing layer 209. A first impurity semiconductor layer 211 and a protective layer 215 are formed on the protective layer 601. The protective layer 601 is obtained by, for example, patterning an inorganic protective film deposited by CVD. The presence of the protective layer 601 further suppresses a reverse dark current in the radiation detection apparatus 600. When etching and dividing a semiconductor layer 220, the protective layer 601 functions as an etching stopper layer, and the formation of a leakage path arising from etching of the organic material of the planarizing layer 209 can be suppressed.

Even in the radiation detection apparatus 600, the residual charge can be reduced by forming a conversion element 111 so as to satisfy both inequalities (1) and (2) described above. The definitions of the variables in inequalities (1) and (2) in the radiation detection apparatus 600 are the same as those in the radiation detection apparatus 100 except that the length $D_{L1}$ and the length $D_{L2}$ have different values in the radiation detection apparatus 600, as shown in FIG. 6.

FIG. 7 shows experimental results when the radiation detection apparatus in which the parameters of inequalities (1) and (2) were set to various values was installed in a laboratory at room temperature (25° C.), and the residual charge 10 µs after a switching element 112 was turned on was measured. The residual charge was 1.3% in the radiation detection apparatus 600 satisfying both inequalities (1) and (2). The residual charge was 3.5% in the first comparative example in which inequality (2) was satisfied but inequality (1) was not satisfied. The residual charge was 2.7% in the second comparative example in which inequality (1) was satisfied but inequality (2) was not satisfied. If the radiation detection apparatus 600 satisfies both inequalities (1) and (2), the residual charge 10 µs after the switching element connected to the conversion element is turned on can become equal to or lower than 2%.

In the arrangement shown in FIG. 6, tunneling of charges readily occurs at a portion, in contact with side surface of the first electrode 210, of the protective layer 601. Hence, by setting $D_{L2}$ to be 5 nm, as in the radiation detection apparatus 100, generation of a leakage current on the side surface of the semiconductor layer 220 can be suppressed. By setting the length $D_{L2}$ to be equal to or larger than 1 µm, the current density of the reverse dark current can be suppressed to be equal to or lower than $10^{-10}$ A/mm², as shown in FIG. 8.

Figure 9:
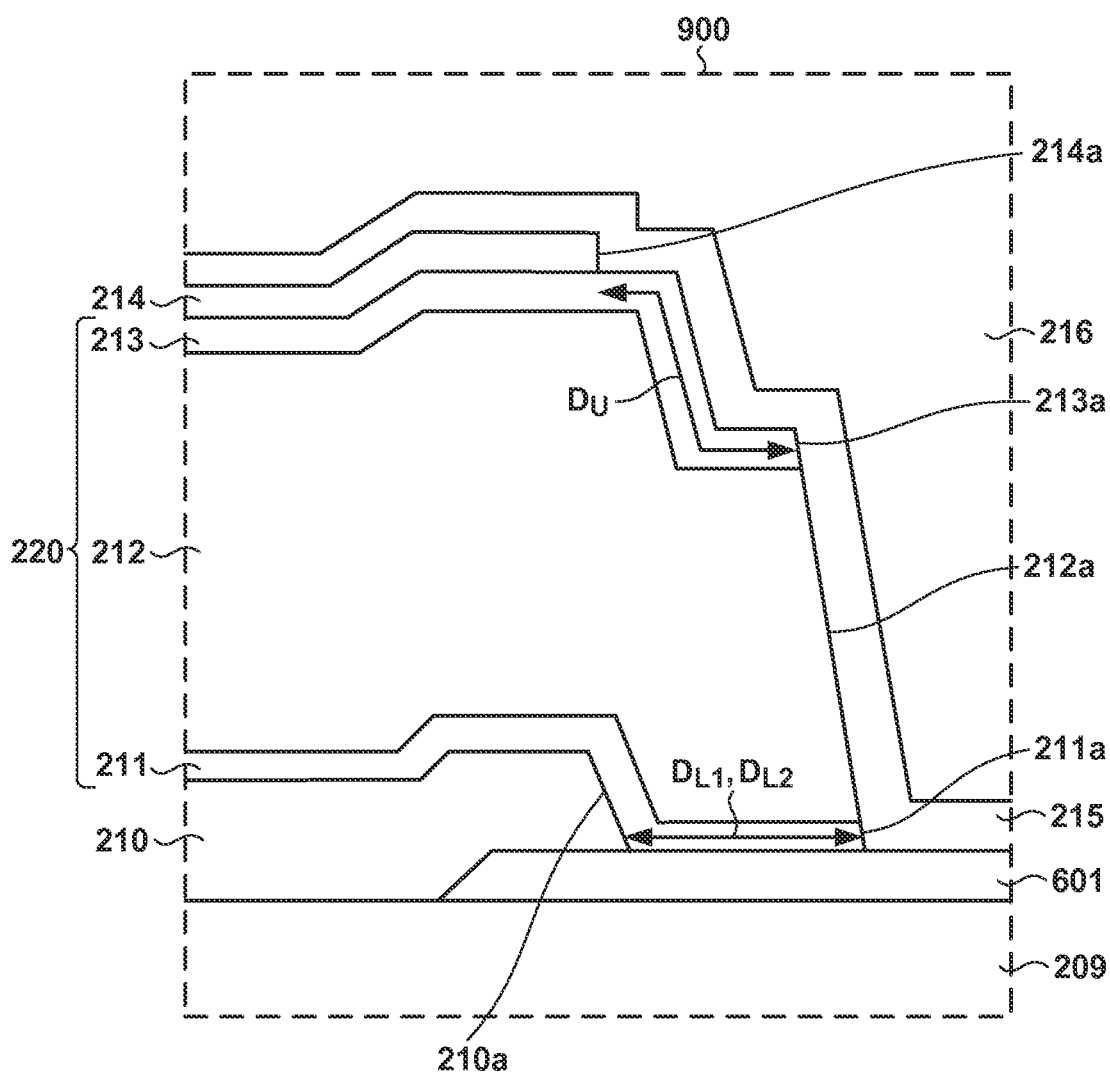
FIG. 9 is a partial schematic sectional view of one pixel of a radiation detection apparatus according to some embodiments.

A radiation detection apparatus 900 according to some embodiments will be explained with reference to FIG. 9. FIG. 9 is a schematic sectional view showing a portion, corresponding to the region 200 in FIG. 3, of the radiation detection apparatus 900. The radiation detection apparatus 900 is different from the radiation detection apparatus 600 in the structure of the portion shown in FIG. 9. The remaining portion of the radiation detection apparatus 900 may be the same as that of the radiation detection apparatus 600, and a repetitive description will be omitted.

The radiation detection apparatus 900 is different from the radiation detection apparatus 600 in the positional relationship between a protective layer 601 and a first electrode 210. The protective layer 601 covers a portion of a planarizing layer 209 at the boundary of a pixel 110. The first electrode 210 is formed to cover the end portion of the protective layer 601.

Even in the radiation detection apparatus 900, the residual charge 10 µs after the switching element connected to the conversion element is turned on can become equal to or lower than 2% by forming a conversion element 111 so as to satisfy both inequalities (1) and (2) described above. The definitions of the variables in inequalities (1) and (2) in the radiation detection apparatus 900 are the same as those in the radiation detection apparatus 100. The length $D_{L1}$ and the length $D_{L2}$ are equal to each other.

By setting $D_{L2}$ to be 5 nm, as in the radiation detection apparatus 100, generation of a leakage current on the side surface of the semiconductor layer 220 can be suppressed. By setting the length $D_{L2}$ to be equal to or larger than 1 µm, the current density of the reverse dark current can be suppressed to be equal to or lower than $10^{-10}$ A/m².

Figure 10:
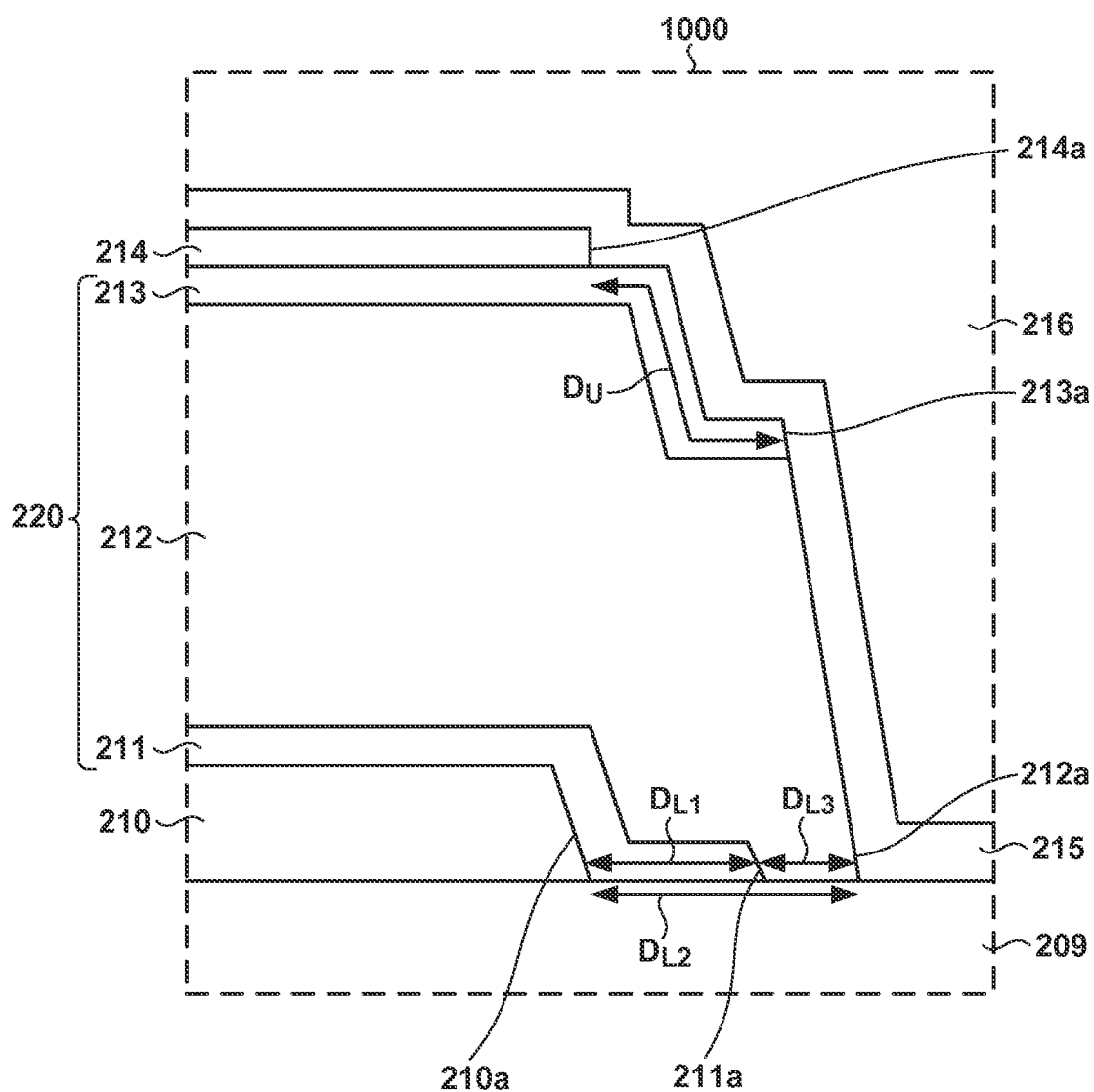
FIG. 10 is a partial schematic sectional view of one pixel of a radiation detection apparatus according to some embodiments.

A radiation detection apparatus 1000 according to some embodiments will be explained with reference to FIG. 10. FIG. 10 is a schematic sectional view showing a portion, corresponding to the region 200 in FIG. 3, of the radiation detection apparatus 1000. The radiation detection apparatus 1000 is different from the radiation detection apparatus 100 in the structure of the portion shown in FIG. 10. The remaining portion of the radiation detection apparatus 1000 may be the same as that of the radiation detection apparatus 100, and a repetitive description will be omitted.

In the radiation detection apparatus 1000, a periphery 212a of an intrinsic semiconductor layer 212 is positioned outside a periphery 211a of a first impurity semiconductor layer 211. In other words, the first impurity semiconductor layer 211 and a protective layer 215 are separated from each other by the intrinsic semiconductor layer 212.

In the radiation detection apparatus 1000, electrons generated near the periphery 212a of the intrinsic semiconductor layer 212 are influenced not only by the parasitic resistance of the first impurity semiconductor layer 211 but also by the parasitic resistance of the intrinsic semiconductor layer 212 when the electrons are collected to a first electrode 210. In the radiation detection apparatus 1000, therefore, a conversion element 111 is so formed as to satisfy inequality (8) in addition to the above-described inequalities (1) and (2):

$$\{D_{L1}/(4\times P)\}\times R_{\square L1}+\{D_{L3}/(4\times P)\}\times R_{\square L3}<5\times R_{on} \quad (8)$$

where $D_{L3}$ is the length from the periphery of the intrinsic semiconductor layer 212 to the periphery 211a of the first impurity semiconductor layer 211, and $R_{\square L3}$ is the sheet resistance of the intrinsic semiconductor layer 212. The definitions of the remaining variables are the same as those in the radiation detection apparatus 100. As long as inequality (8) is satisfied, inequality (1) is automatically satisfied. In the radiation detection apparatus 1000, the residual charge 10 µs after the switching element connected to the conversion element is turned on can become equal to or lower than 2% by forming the conversion element 111 so as to satisfy both inequalities (8) and (2) described above.

By setting $D_{L2}$ to be 5 nm, as in the radiation detection apparatus 100, generation of a leakage current on the side surface of a semiconductor layer 220 can be suppressed. By setting the length $D_{L2}$ to be equal to or larger than 1 µm, the current density of the reverse dark current can be suppressed to be equal to or lower than $10^{-10}$ A/mm$^2$.

Figure 11:
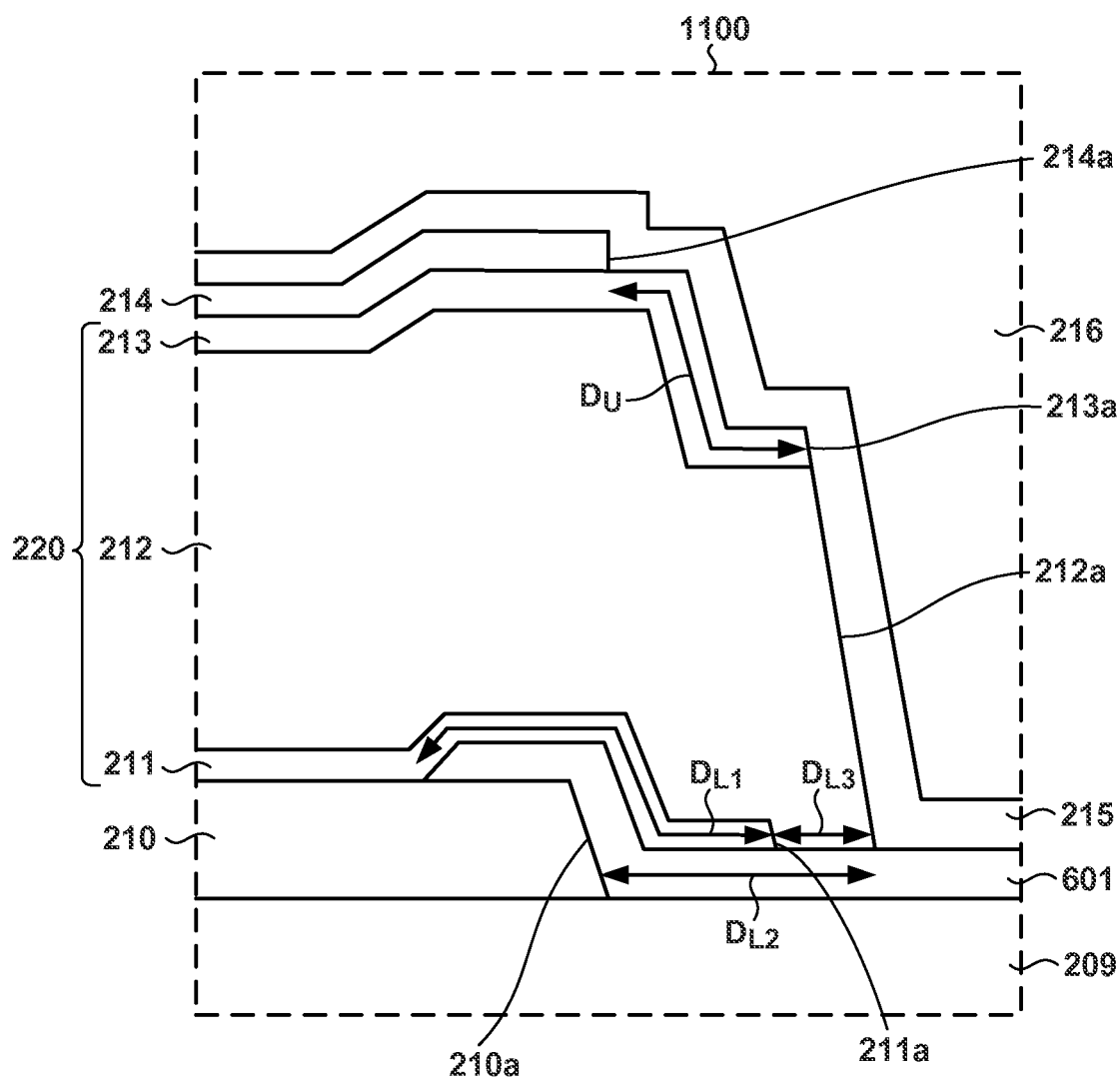
FIG. 11 is a partial schematic sectional view of one pixel of a radiation detection apparatus according to some embodiments.

A radiation detection apparatus 1100 according to some embodiments will be explained with reference to FIG. 11. FIG. 11 is a schematic sectional view showing a portion, corresponding to the region 200 in FIG. 3, of the radiation detection apparatus 1100. In the radiation detection apparatus 1100, a protective layer 601 described with reference to FIG. 6 is further arranged in the arrangement in which a periphery 212a of an intrinsic semiconductor layer 212 is positioned outside a periphery 211a of a first impurity semiconductor layer 211, as in the radiation detection apparatus 1000. Even in the radiation detection apparatus 1100, the residual charge 10 µs after the switching element connected to the conversion element is turned on can become equal to or lower than 2% by forming a conversion element 111 so as to satisfy both inequalities (8) and (2) described above. By setting $D_{L2}$ to be 5 nm, as in the radiation detection apparatus 100, generation of a leakage current on the side surface of a semiconductor layer 220 can be suppressed. By setting the length $D_{L2}$ to be equal to or larger than 1 µm, the current density of a reverse dark current can be suppressed to be equal to or lower than $10^{-10}$ A/mm$^2$.

Figure 12:
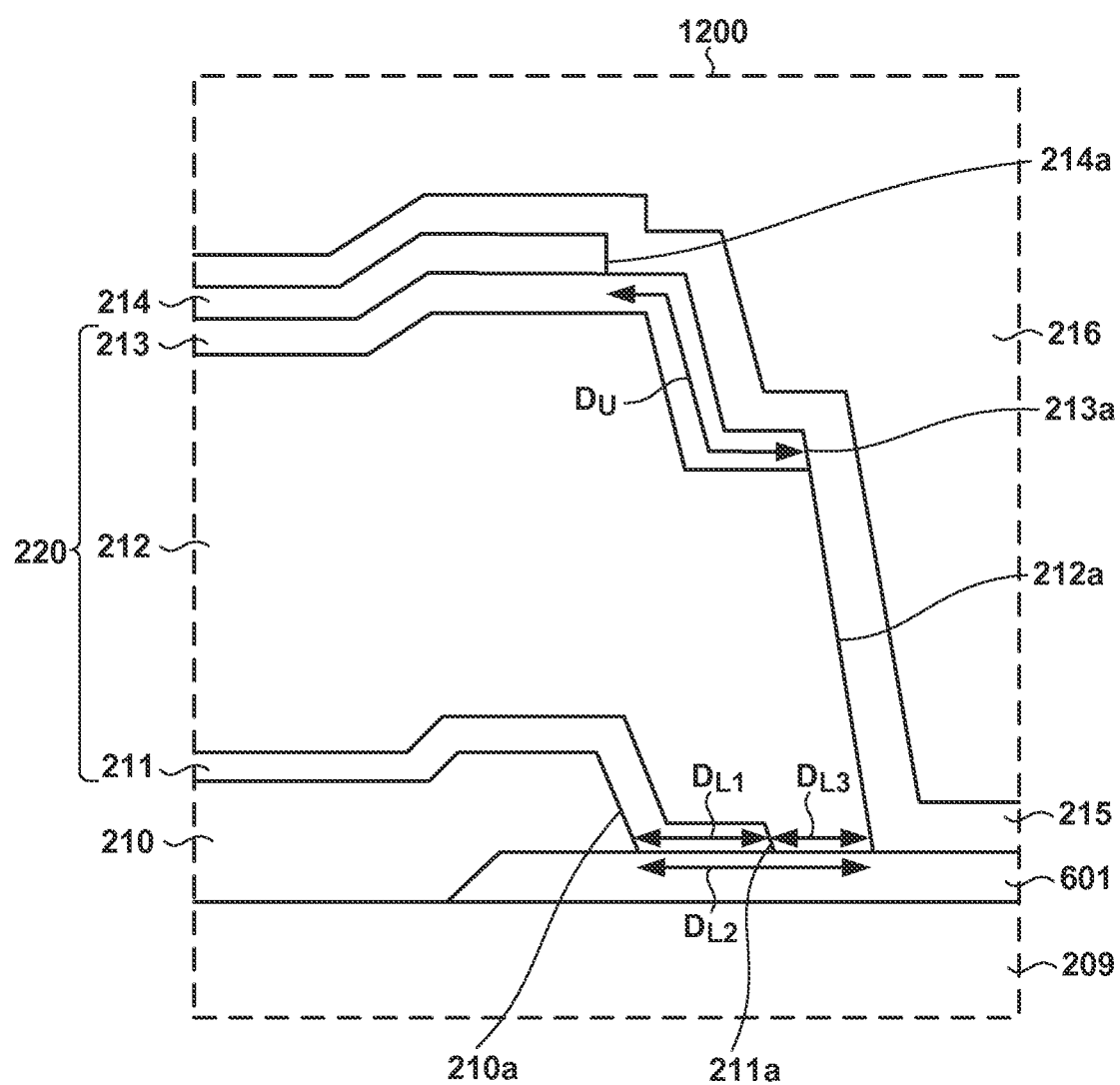
FIG. 12 is a partial schematic sectional view of one pixel of a radiation detection apparatus according to some embodiments.

A radiation detection apparatus 1200 according to some embodiments will be explained with reference to FIG. 12. FIG. 12 is a schematic sectional view showing a portion, corresponding to the region 200 in FIG. 3, of the radiation detection apparatus 1200. In the radiation detection apparatus 1200, a protective layer 601 described with reference to FIG. 7 is further arranged in the arrangement in which a periphery 212a of an intrinsic semiconductor layer 212 is positioned outside a periphery 211a of a first impurity semiconductor layer 211, as in the radiation detection apparatus 1000. Even in the radiation detection apparatus 1200, the residual charge 10 µs after the switching element connected to the conversion element is turned on can become equal to or lower than 2% by forming a conversion element 111 so as to satisfy both inequalities (8) and (2) described above. By setting $D_{L2}$ to be 5 nm, as in the radiation detection apparatus 100, generation of a leakage current on the side surface of a semiconductor layer 220 can be suppressed. By setting the length $D_{L2}$ to be equal to or larger than 1 µm, the current density of a reverse dark current can be suppressed to be equal to or lower than $10^{-10}$ A/mm$^2$.

Figure 13:
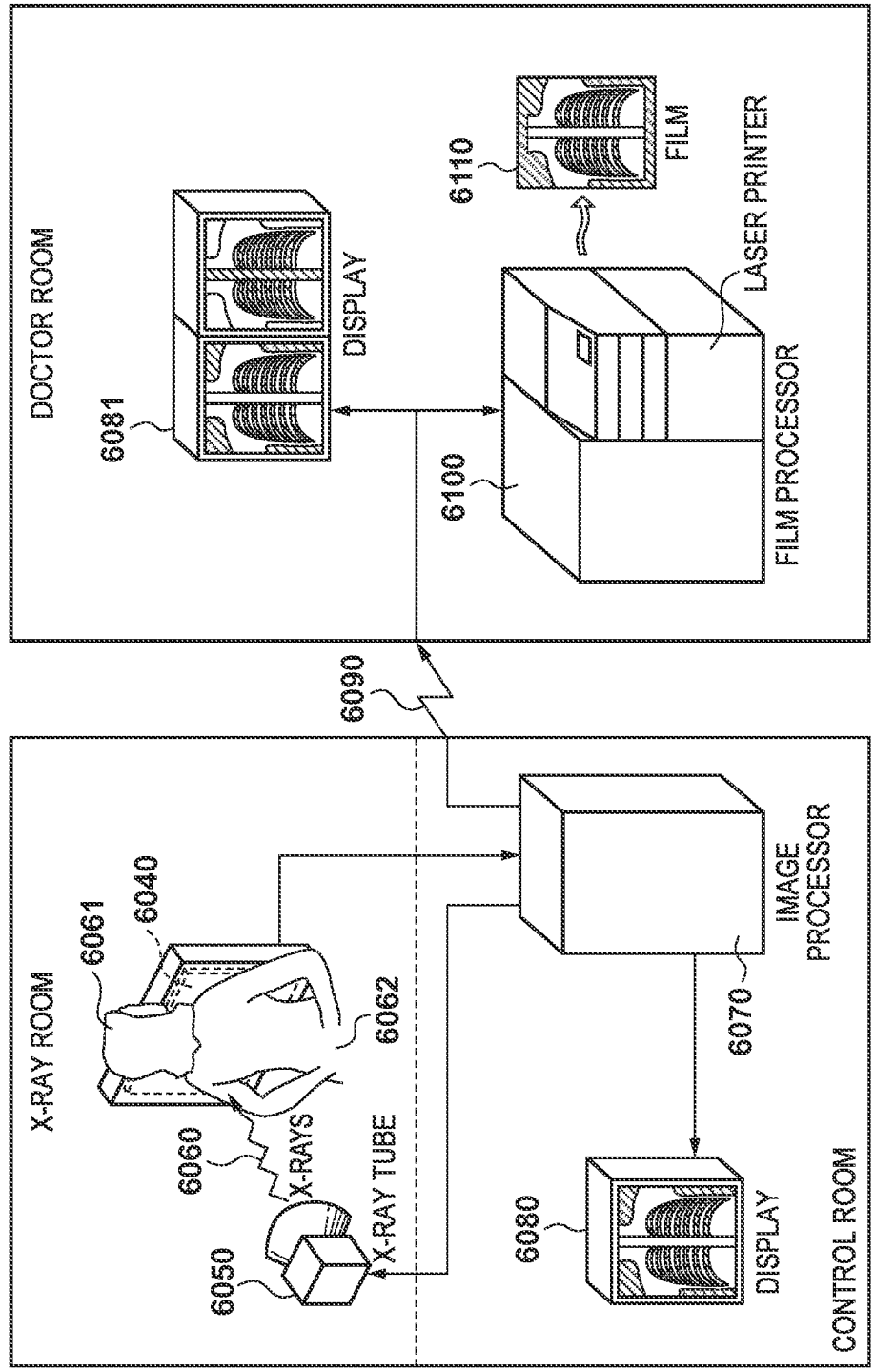
FIG. 13 is a view of the configuration of a radiation detection system according to some embodiments.

FIG. 13 is a view showing an application example of the radiation detection apparatus according to the present invention to an X-ray diagnostic system (radiation detection system). X-rays 6060 generated as a radiation by an X-ray tube 6050 (radiation source) pass through a chest 6062 of an object or patient 6061 and enter a detection apparatus 6040 in which a scintillator is arranged at the top of the detection apparatus according to the present invention. Here, the detection conversion apparatus in which the scintillator is arranged at the top constitutes the radiation detection apparatus. The incident X-rays include information about the inside of the body of the patient 6061. The scintillator emits light in correspondence with the entrance of the X-rays, and the light is photoelectrically converted, obtaining electrical information. This information is converted into a digital signal, undergoes image processing by an image processor 6070 serving as a signal processor, and can be observed on a display 6080 serving as a display unit in a control room. Note that the radiation detection system includes at least the detection apparatus, and the signal processor that processes a signal from the detection apparatus.

This information can be transferred to a remote place by a transmission processor such as a telephone line 6090, and can be displayed on a display 6081 serving as a display unit in a doctor room or the like at another place, or can be saved on a recording unit such as an optical disk. Even a doctor at the remote place can make a diagnosis. A film processor 6100 serving as a recording unit can also record the information on a film 6110 serving as a recording medium.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-026896, filed Feb. 14, 2014 and 2015-001889, filed Jan. 7, 2015, which are hereby incorporated by reference herein in their entirety.

What is claimed is:

1. A radiation detection apparatus including a plurality of pixels, the apparatus comprising:
conversion elements including a first electrode, a semiconductor layer, and a second electrode that are divided for each pixel;
switching elements electrically connected to the first electrodes; and
a first insulating layer that separates the conversion elements of adjacent pixels,
wherein the semiconductor layer is located between the first electrode and the second electrode,
a periphery of the semiconductor layer is located outside a periphery of the first electrode and a periphery of the second electrode,
the semiconductor layer includes a first impurity semiconductor layer including a portion in contact with the first electrode, a second impurity semiconductor layer including a portion in contact with the second electrode, and an intrinsic semiconductor layer located between the first impurity semiconductor layer and the second impurity semiconductor layer, and
a length $D_{L1}$ from a periphery of the first impurity semiconductor layer along the first impurity semiconductor layer up to the portion, in contact with the first electrode, of the first impurity semiconductor layer, a length $D_U$ from a periphery of the second impurity semiconductor layer along the second impurity semiconductor layer up to the portion, in contact with the second electrode, of the second impurity semiconductor layer, a sheet resistance $R_{\square L1}$ of the first impurity semiconductor layer, a sheet resistance $R_{\square U}$ of the second impurity semiconductor layer, a pixel pitch P of the plurality of pixels, and an ON resistance $R_{on}$ of the switching element are defined to set a residual charge 10 µs after the switching element is turned on to be not higher than 2%.

2. The apparatus according to claim 1, wherein $$\{D_{L1}/(4\times P)\}\times R_{\square L1}<5\times R_{on}, \text{ and}$$

$$\{D_U/(4\times P)\}\times R_{\square U}<100\times R_{on}$$

are satisfied.

3. The apparatus according to claim 1, wherein a length from the periphery of the first electrode to the periphery of the semiconductor layer is not smaller than 5 nm.

4. The apparatus according to claim 1, wherein a length from the periphery of the first electrode to the periphery of the semiconductor layer is not smaller than 1 µm.

5. The apparatus according to claim 1, wherein a length from the periphery of the second electrode to the periphery of the semiconductor layer is not smaller than 5 nm.

6. The apparatus according to claim 1, wherein a length from the periphery of the second electrode to the periphery of the semiconductor layer is not smaller than 1 µm.

7. The apparatus according to claim 1, wherein the periphery of the first impurity semiconductor layer contacts the first insulating layer.

8. The apparatus according to claim 1, wherein the first impurity semiconductor layer and the first insulating layer are separated from each other by the intrinsic semiconductor layer.

9. The apparatus according to claim 8, wherein letting $D_{L3}$ be a length from the periphery of the first impurity semiconductor layer to a periphery of the intrinsic semiconductor layer, and $R_{\square L3}$ be a sheet resistance of the intrinsic semiconductor layer, $$\{D_{L1}/(4\times P)\}\times R_{\square L1}+\{D_{L3}/(4\times P)\}\times R_{\square L3}<5\times R_{on}$$

is further satisfied.

10. The apparatus according to claim 1, further comprising a second insulating layer that separates the periphery of the first electrode and the first impurity semiconductor layer from each other.

11. The apparatus according to claim 1, further comprising a scintillator layer that is arranged on the plurality of pixels and converts a radiation into light of a wavelength detectable by the conversion element.

12. A radiation detection system comprising:
a radiation detection apparatus defined in claim 1; and
a signal processing unit for processing a signal obtained by the radiation detection apparatus.

* * * * *